(12) United States Patent
Wu

(10) Patent No.: US 10,869,606 B2
(45) Date of Patent: Dec. 22, 2020

(54) METHOD AND APPARATUS FOR HUMAN HEALTH EVALUATION

(71) Applicant: Jiangsu Huaben Health Life Science and Technology Co., Ltd., Jiangsu (CN)

(72) Inventor: Ben Jun Wu, Fort Erie (CA)

(73) Assignee: Jiangsu Huaben Health Life Science and Technology Co., Ltd.

( * ) Notice: Subject to any disclaimer, the term of this patent is extended or adjusted under 35 U.S.C. 154(b) by 727 days.

(21) Appl. No.: 15/588,579

(22) Filed: May 5, 2017

(65) Prior Publication Data
US 2018/0317778 A1 Nov. 8, 2018

(51) Int. Cl.
| | |
|---|---|
| A61B 5/0205 | (2006.01) |
| A61B 5/024 | (2006.01) |
| G16H 50/20 | (2018.01) |
| A61B 5/022 | (2006.01) |
| G16H 40/63 | (2018.01) |
| G16H 50/30 | (2018.01) |

(Continued)

(52) U.S. Cl.
CPC .......... *A61B 5/0205* (2013.01); *A61B 5/022* (2013.01); *A61B 5/02438* (2013.01); *A61B 5/08* (2013.01); *A61B 5/201* (2013.01); *A61B 5/4064* (2013.01); *A61B 5/416* (2013.01); *A61B 5/4244* (2013.01); *A61B 5/4854* (2013.01); *A61B 5/6824* (2013.01); *A61B 5/7267* (2013.01); *A61B 5/7275* (2013.01); *G16H 40/63* (2018.01); *G16H 50/20* (2018.01); *G16H 50/30* (2018.01); *A61B 5/021* (2013.01); *A61B 5/024* (2013.01)

(58) Field of Classification Search
None
See application file for complete search history.

(56) References Cited

U.S. PATENT DOCUMENTS

| | | | | |
|---|---|---|---|---|
| 4,320,767 A | * | 3/1982 | Villa-Real | A61B 5/021 600/493 |
| 6,447,457 B1 | * | 9/2002 | Forstner | A61B 5/022 600/485 |

(Continued)

OTHER PUBLICATIONS

Patel, Niitt and Louis Alarcon, "Blunt Splenic Trauma," The American Association for the Surgery of Trauma, http://www.aast.org/GeneralInforrnation/BluntSplenicTrauma.aspx , May 2012, pp. 1-3 (Year: 2012).*

*Primary Examiner* — Matthew Kremer
(74) *Attorney, Agent, or Firm* — Han IP PLLC; Andy M. Han

(57) ABSTRACT

Techniques and examples pertaining to evaluating a health condition of an aspect of a patient are described. A method for evaluating the health condition of the aspect of the patient may involve obtaining successive measurement readings of a vital sign concurrently from both a left arm and a right arm of the patient for a plurality of times. The method may also involve calculating a characteristic value based on the measurement readings. The method may also involve designating a health indicator based on the characteristic value and a standard value associated with the aspect of the patient, such that the health indicator serves as an indication of the health condition of the aspect of the patient. The aspect of the patient may be a body organ of the patient. The method may further involve diagnosing the patient based on the health indicator.

6 Claims, 3 Drawing Sheets

(51) Int. Cl.
*A61B 5/08* (2006.01)
*A61B 5/20* (2006.01)
*A61B 5/00* (2006.01)
*A61B 5/021* (2006.01)

(56) References Cited

U.S. PATENT DOCUMENTS

| | | | |
|---|---|---|---|
| 2005/0075542 A1* | 4/2005 | Goldreich | A61B 5/0205 600/300 |
| 2007/0094048 A1* | 4/2007 | Grichnik | G16H 50/30 705/2 |
| 2013/0144176 A1* | 6/2013 | Lec | A61B 5/0002 600/485 |
| 2014/0276783 A1* | 9/2014 | Srivastava | A61N 7/022 606/41 |
| 2016/0296155 A1* | 10/2016 | Helfenbein | A61B 5/742 |
| 2017/0156668 A1* | 6/2017 | Husain | A61B 5/684 |

* cited by examiner

METHOD AND APPARATUS FOR HUMAN HEALTH EVALUATION

TECHNICAL FIELD

The present disclosure generally relates to human health evaluation and, more particularly, to a method and an apparatus for evaluating human health by concurrently taking blood pressure readings from both arms of a patient.

BACKGROUND

Modern Western medicine (MWM) heavily relies on various medical diagnostic or examination equipment. A MWM practitioner typically diagnoses a patient by analyzing or otherwise examining medical data of the patient collected using medical diagnostic or examination equipment. For example, in order to diagnose whether a patient may have a fatty liver or even cirrhosis, a MWM practitioner may examine a series of abdominal ultrasound pictures of the patient measured by an ultrasound machine. In contrast, modern diagnostic or examination equipment is hardly utilized by a practitioner of traditional Chinese medicine (TCM), originated in ancient China and having evolved over thousands of years. A TCM practitioner typically diagnoses a patient using techniques of "pulse diagnosis". The techniques of pulse diagnosis may be viewed as a method for evaluating a health condition of one or more aspects of a patient. Specifically, the TCM practitioner may use his or her hand to physically touch the patient and feel, observe or otherwise examine a "pulse" of the patient. Based on a pattern of the pulse (e.g., a strength or a frequency of the pulse observed over a period of time), the TCM practitioner may be able to diagnose a clinical disease (hereinafter "a disease") or a subclinical disease (hereinafter "a sub-disease") of the patient. the TCM practitioner may further prescribe a medication order for treating the clinical or subclinical disease, or at least for easing one or more symptoms thereof.

An often-criticized feature of the pulse diagnosis adopted by TCM resides in its inherent subjectivity of pulse diagnosis. For example, a description of the pulse pattern (i.e., the pattern of the pulse of the patient) is rather abstract, and lacks an objective definition. Therefore, different TCM practitioners may feel the pulse of the patient differently, and may thus divide in their opinions regarding a diagnosis of a disease/sub-disease the patient may have, let alone a treatment plan for curing the disease/sub-disease.

Another often-mentioned drawback of the pulse diagnosis used by TCM is a lack of an ability to associated, in a more direct way, the pulse pattern with a specific body organ that may exhibit a health problem. That is, based solely on the pulse pattern, which is more like a combinational health indicator, it may be difficult for the TCM practitioner to pinpoint a specific body organ that may be malfunctioning or experiencing a less-than-healthy condition.

Therefore, an objective and more direct way of evaluating a health condition of one or more aspects of a patient is required.

SUMMARY

This section is for the purpose of summarizing some aspects of the present disclosure and to briefly introduce some preferred embodiments. Simplifications or omissions in this section as well as in the abstract or the title of this description may be made to avoid obscuring the purpose of this section, the abstract and the title. Such simplifications or omissions are not intended to limit the scope of the present disclosure.

According to an aspect of the present disclosure, a method for evaluating a health condition of an aspect of a patient is disclosed. The method involves obtaining successive measurement readings of a vital sign concurrently from both a left arm and a right arm of the patient for a plurality of times. The method also involves calculating a characteristic value based on the measurement readings. The method further involves designating a health indicator based on the characteristic value and a standard value associated with the aspect of the patient, the health indicator being an indication of the health condition of the aspect of the patient.

In some embodiments, the aspect of the patient is a heart of the patient, the vital sign is a pulse rate, and the characteristic value is either a difference between, or an average of, a maximum value and a minimum value of the measurement readings of the pulse rate taken from both the left and right arms of the patient. In the case that the characteristic value is the difference between the maximum value and the minimum value, the standard value is 3 beats per minute, and the health indicator is designated based on the difference represented using the standard value. In the case that the characteristic value is the average of the maximum value and the minimum value, the standard value is 65 beats per minute, and the health indicator is designated based on a percentage by which the average is away from standard value.

In some embodiments, the aspect of the patient is a liver of the patient, the vital sign is a diastolic blood pressure, and the characteristic value is either a difference between, or an average of, a maximum value and a minimum value of the measurement readings of the diastolic blood pressure taken from the right arm of the patient. In the case that the characteristic value is the difference between the maximum value and the minimum value, the standard value is 3 millimeter of mercury (mmHg), and the health indicator is designated based on the difference represented using the standard value. In the case that the characteristic value is the average of the maximum value and the minimum value, the standard value is 58 mmHg, and the health indicator is designated based on a percentage by which the average is away from standard value.

In some embodiments, the aspect of the patient is a spleen of the patient, the vital sign is a diastolic blood pressure, and the characteristic value is either a difference between, or an average of, a maximum value and a minimum value of the measurement readings of the diastolic blood pressure taken from the left arm of the patient. In the case that the characteristic value is the difference between the maximum value and the minimum value, the standard value is 3 mmHg, and the health indicator is designated based on the difference represented using the standard value. In the case that the characteristic value is the average of the maximum value and the minimum value, the standard value is 58 mmHg, and the health indicator is designated based on a percentage by which the average is away from standard value.

In some embodiments, the aspect of the patient is a lung or a brain of the patient, the vital sign is a systolic blood pressure, and the characteristic value is either a difference between, or an average of, a maximum value and a minimum value of the measurement readings of the systolic blood pressure taken from the left arm of the patient. In the case that the characteristic value is the difference between the maximum value and the minimum value, the standard value is 3 mmHg, and the health indicator is designated based on the difference represented using the standard value. In the case that the characteristic value is the average of the maximum value and the minimum value, the standard value is 100 mmHg, and the health indicator is designated based on a percentage by which the average is away from standard value.

In some embodiments, the aspect of the patient is a kidney of the patient, the vital sign is a systolic blood pressure, and the characteristic value is either a difference between, or an average of, a maximum value and a minimum value of the measurement readings of the systolic blood pressure taken from the right arm of the patient. In the case that the characteristic value is the difference between the maximum value and the minimum value, the standard value is 3 mmHg, and the health indicator is designated based on the difference represented using the standard value. In the case that the characteristic value is the average of the maximum value and the minimum value, the standard value is 100 mmHg, and the health indicator is designated based on a percentage by which the average is away from standard value.

In some embodiments, the aspect of the patient is an overall body of the patient, the vital sign includes a systolic blood pressure and a diastolic blood pressure, and the characteristic value is a ratio of the measurement readings of the systolic blood pressure to the measurement readings of the diastolic blood pressure taken from both the left and right arms. The standard value is 1.72, and the health indicator is designated based on a percentage by which the ratio is away from the standard value.

According to another aspect of the present disclosure, an apparatus is disclosed for evaluating a health condition of an aspect of a patient. The apparatus includes a memory capable of storing one or more sets of instructions and one or more standard values. The apparatus also includes a processor coupled to execute the one or more sets of instructions stored in the memory such that, upon executing the one or more sets of instructions, the processor may calculate a characteristic value based on measurement readings of a vital sign concurrently obtained from either or both of a left arm and a right arm of a patient. In addition, the processor may designate a health indicator based on the characteristic value and at least one of the one or more standard values, the health indicator being an indication of a health condition of an aspect of the patient.

BRIEF DESCRIPTION OF THE DRAWINGS

These and other features, aspects, and advantages of the present disclosure will become better understood with regard to the following description, appended claims, and accompanying drawings where:

DETAILED DESCRIPTION OF THE PREFERRED EMBODIMENTS

The detailed description of the present disclosure is presented largely in terms of procedures, steps, logic blocks, processing, or other symbolic representations that directly or indirectly resemble the operations of devices or systems contemplated in the present disclosure. These descriptions and representations are typically used by those skilled in the art to most effectively convey the substance of their work to others skilled in the art.

Reference herein to "one embodiment" or "an embodiment" means that a particular feature, structure, or characteristic described in connection with the embodiment can be comprised in at least one embodiment of the present disclosure. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams or the use of sequence numbers representing one or more embodiments of the present disclosure do not inherently indicate any particular order nor imply any limitations in the present disclosure.

To make the above objects, features and advantages of the present disclosure more obvious and easier to understand, the present disclosure is further described in detail below using various embodiments.

Figure 1:
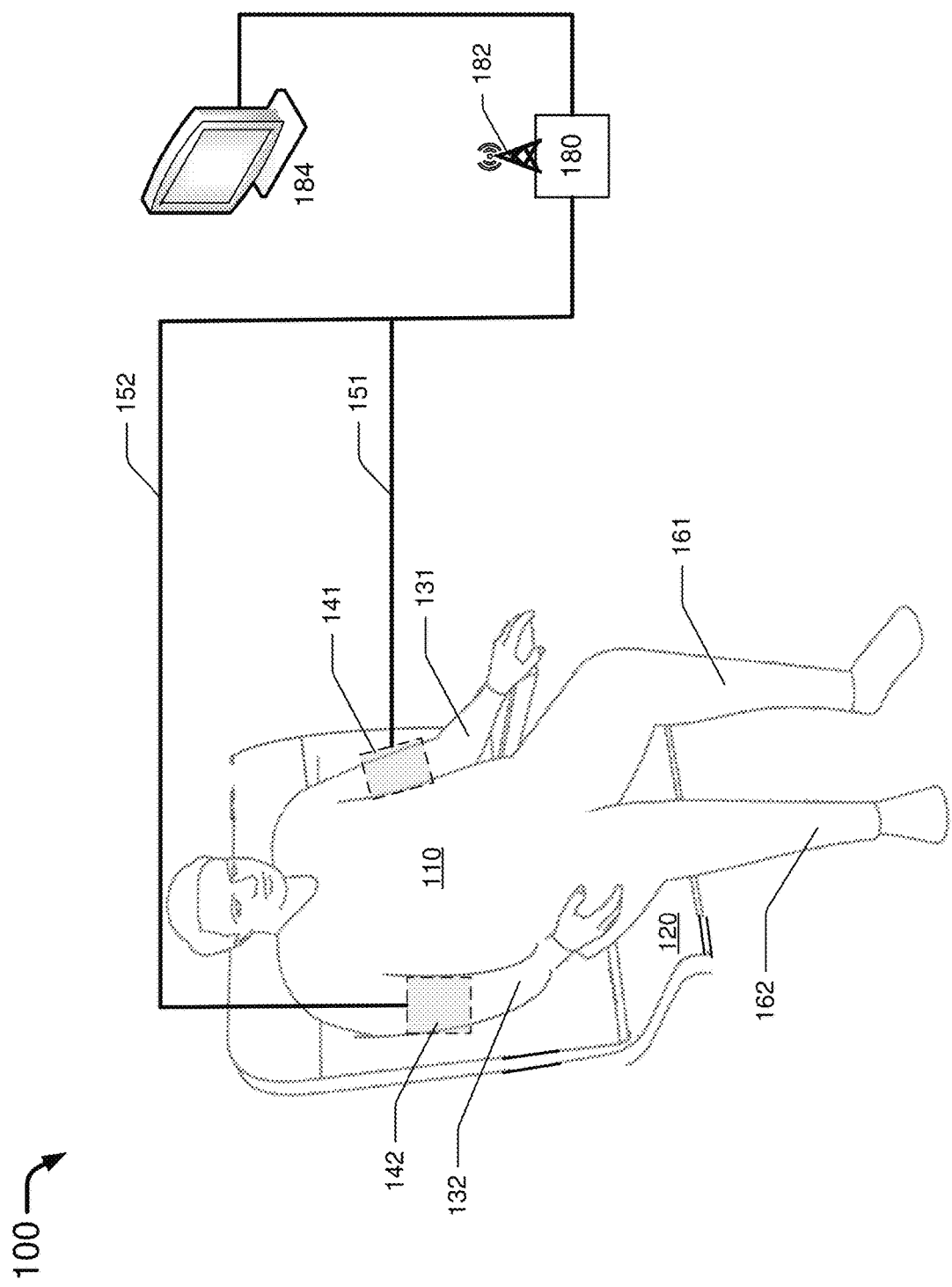
FIG. 1 is a diagram depicting an example implementation in accordance with an embodiment of the present disclosure.

As mentioned above, it is desired for a TCM practitioner to evaluate a health condition of one or more aspects of a patient using a more objective method than the pulse diagnosis techniques that have been traditionally adopted by TCM. In particular, it is desired that the TCM practitioner is enabled to evaluate the health condition of one or more body organs of the patient. FIG. 1 depicts an example implementation 100 through which these desired purposes may be achieved. Under implementation 100, a patient 110 may be seated in a chair 120, with the patient's left arm 131 and right arm 132 relaxed and laying low. In addition, patient 110 may wear a vital sign sensor 141 on left arm 131 and a vital sign sensor 142 on right arm 132. Vital sign sensor 141 and vital sign sensor 142 may be communicatively coupled through communication links 151 and 152, respectively, to a processor 180. Alternatively or additionally, each of vital sign sensors 141 and 142 may be wirelessly coupled to processor 180 through wireless transceiver 182. Processor 180 may control each of vital sign sensors 141 and 142 to measure one or more vital signs of patient 110. In some embodiments, processor 180 may communicate with patient 110 through communication console 184. As an example, processor 180 may instruct patient 110 through communication console 184 to remain relaxed in seat 120 until the one or more vital signs of patient 110 have been measured successfully by vital sign sensors 141 and 142. As another example, processor 180 may instruct patient 110 through communication console 184 not to cross the legs 161 and 162, lest the one or more vital signs as measured by vital sign sensors 141 and 142 may not be accurate.

In some embodiments, each of vital sign sensors 141 and 142 may be a blood pressure monitor, and the one or more vital signs measured by vital sign sensors 141 and 142 may include one or more of a pulse rate (i.e., a heart rate), a diastolic blood pressure, a systolic blood pressure, and the like, of patient 110. It is worth noting that it is essential for the one or more vital signs to be measured substantially concurrently from left arm 131 and right arm 132 using vital sign sensors 141 and 142, respectively. As shown in FIG. 1, patient 110 is wearing vital sign sensors 141 and 142 simultaneously such that processor 180 is able to measure one or more of the pulse rate, the diastolic blood pressure and the diastolic blood pressure of concurrently using vital sign sensors 141 and 142.

The concurrent measurement of the one or more vital signs from left and right arms 131 and 132 may be repeated successively for one or more times. Table 1 shows an example measurement readings of the vital signs of patient 110 for 5 successive measurement runs (i.e., the measurement is repeated for 5 times in a row). The measurement readings may be obtained by processor 180 using vital sign sensors 141 and 142 through communication links 151 and 152 or wireless transceiver 182:

TABLE 1

| Meas. No. | L-systolic | L-diastolic | L-PR | R-systolic | R-diastolic | R-PR |
|---|---|---|---|---|---|---|
| 1 | 133 | 83 | 74 | 126 | 75 | 79 |
| 2 | 125 | 74 | 72 | 122 | 71 | 73 |
| 3 | 126 | 74 | 70 | 124 | 73 | 71 |
| 4 | 122 | 78 | 72 | 120 | 79 | 72 |
| 5 | 132 | 82 | 72 | 123 | 76 | 74 |

As shown in Table 1, the vital sign measurement of patient 110 has been carried out for 5 successive times. The columns labeled as "L-systolic", "L-diastolic" and "L-PR" represent the systolic blood pressure, the diastolic blood pressure, and the pulse rate of patient 110, respectively, that are measured successively by vital sign sensor 141 worn on left arm 131, whereas the columns labeled as "R-systolic", "R-diastolic" and "R-PR" represent the systolic blood pressure, the diastolic blood pressure, and the pulse rate of patient 110, respectively, that are measured successively by vital sign sensor 142 worn on right arm 132. For each row in Table 1 (i.e., for each of the 5 measurement runs), the measurement readings recorded in "L-systolic", "L-diastolic" and "L-PR" columns are obtained concurrently with the measurement readings recorded in "R-systolic", "R-diastolic" and "R-PR" columns.

To evaluate a health condition of an aspect (e.g., a body organ, such as a heart, a liver, a spleen, a lung, a brain or a kidney) of patient 110, measurement readings as shown in Table 1 may be utilized, at least partly, to calculate one or more characteristic values, which may be subsequently compared to one or more standard values. The standard values represent a golden standard, or a desired, healthy condition of the aspect. The extent to which the characteristic values deviate from the standard values indicates how far away the aspect of patient 110 is from the healthy condition of the aspect. A quantified figure of merit, called "health indicator", may be used to indicate or otherwise represent the deviation of the characteristic values from the standard values, giving an estimate of the health condition of the aspect of patient 110.

As a first example, the aspect of patient 110 may be the overall body of patient 110, and the measurement readings of Table 1 may be utilized to designate a health indicator that serves as an indication of a health condition of the overall body of patient 110. Specifically, for each pair of measurement readings of the systolic blood pressure and the diastolic blood pressure obtained from either left arm 131 or right arm 132 of patient 110, a ratio of the measurement reading of the systolic blood pressure to the measurement reading of the diastolic blood pressure, called "S/D ratio", may be calculated. For instance, in the first of the 5 successive measurement runs, L-systolic reads 133 mmHg, while L-diastolic reads 83 mmHg. The S/D ratio can therefore be calculated as 133/83=1.60. Calculating the S/D ratio for each pair of measurement readings of the systolic blood pressure and the diastolic blood pressure in Table 1 results in Table 2:

TABLE 2

| Meas. No. | L-S/D | R-S/D |
|---|---|---|
| 1 | 1.60 | 1.68 |
| 2 | 1.69 | 1.72 |
| 3 | 1.70 | 1.70 |
| 4 | 1.56 | 1.52 |
| 5 | 1.61 | 1.62 |

As shown in Table 2, the column labeled as L-S/D contains the S/D ratio calculated using the measurement readings in columns L-systolic and L-diastolic of Table 1, whereas the column labeled as R-S/D contains the S/D ratio calculated using the measurement readings in columns R-systolic and R-diastolic of Table 1. The average of a maximum value and a minimum value of each of the S/D columns of Table 2 may be used as a characteristic value associated with the overall body of patient 110. That is, using values in L-S/D column, the characteristic value may be calculated as an average of the maximum value 1.70 and the minimum value 1.56 in that column, which is (1.70+1.56)/2=1.63. Similarly, the maximum value and the minimum value for R-S/D column are 1.72 and 1.52, respectively, and the characteristic value based on R-S/D values can thus be calculated as (1.72+1.52)/2=1.62.

For the overall body, the standard value is 1.72. Therefore, it can be calculated that the characteristic value based on L-S/D is about −5% as compared to the standard value (i.e., about 5% less than the standard value 1.72), whereas the characteristic value based on R-S/D is about −6% as compared to the standard value (i.e., about 6% less than the standard value 1.72). The deviation may be calculated by equation (1) as shown below:

$$\text{Deviation}=((\text{Characteristic Value}/\text{Standard Value})-1)\times 100\% \quad (1)$$

Each of the deviation of −5% and −6%, as calculated using equation (1), represents deviation of the characteristic values from the standard value, and the health indicator may be accordingly designated based on the deviation. Specifically, in the first example, if a character value deviates from a corresponding standard value in the positive direction (i.e., deviation is calculated to be equal to or larger than 0) by less than 10%, the health indicator is designated as 0. If the character value deviates from the standard value in the positive direction by 10% or larger but less than 20%, the health indicator is designated as +1. If the character value deviates from the standard value in the positive direction by 20% or larger but less than 30%, the health indicator is designated as +2, and so on. Thus, in a similar way, the health indicator may also be designated as +3, +4, . . . , or +N, where N is a positive integer, depending on how much deviation the characteristic value is as compared to the standard value using equation (1). In the negative direction (i.e., deviation is calculated to be less than 0), the health indicator may be designated in a similar way. That is, if the character value deviates from the standard value in the negative direction by less than 10%, the health indicator is designated as −1. If the character value deviates from the standard value in the negative direction by 10% or larger but less than 20%, the health indicator is designated as −2, and so on. The health indicator may also be designated as −3, −4, . . . , or −10, depending on how much deviation the characteristic value is as compared to the standard value using equation (1). Clearly, the further the health indicator is designated away from 0, the worse the health condition of the aspect of the patient may be.

In the first example, since the deviation is calculated as −5% for L-D/S and −6% for R-D/S per equation (1), the health indicator is designated as −1 for both L-D/S and R-D/S. Given that the health indicator is designated as only −1 for both L-D/S and R-D/S, the overall body of patient 110 is rather healthy, even though the diastolic blood pressure of patient 110 may be slightly higher than desired.

As a second example, the aspect of patient 110 may be the heart of patient 110, and the measurement readings of Table 1 may be utilized to designate a health indicator that serves as an indication of a health condition of the heart of patient 110. Specifically, the characteristic value for the second example may be either a range or an average of the pulse rate readings from both of left arm 131 or right arm 132 of patient 110 as shown in Table 1. The range is defined as a difference between a maximum value and a minimum value among the measurement readings of columns L-PR and R-PR of Table 1, whereas the average is defined as a mean value of the maximum value and the minimum value. According to columns L-PR and R-PR of Table 1, the maximum pulse rate is 79 beats/minutes as measured during the first of the 5 measurement runs from vital sign sensor 142, and the minimum pulse rate is 70 beats/minutes as measured during the third of the 5 measurement runs from vital sign sensor 141. Therefore, the range is calculated as 79−70=9 beats/minute, whereas the average is calculated as (79+70)/2=74.5 beats/minute. For the second example where the aspect of interest is the heart, the standard value for the range is 3 beats/minute, and the standard value for the average is 65 beats/minutes. The deviation of the average from the corresponding standard value may be calculated, using equation (1) above, to be 15% in the positive direction, and thus a corresponding health indicator is accordingly designated as +1. This way for designating the health indicator is similar to that used in the first example, and is applicable to the rest of the examples in the present disclosure when a characteristic value is based on an average of a maximum measurement reading and a minimum measurement reading.

In contrast, the health indicator of the range is designated using a different criterion from that for the average, using equation (2):

$$\text{Health indicator} = \text{floor}(\text{Characteristic Value}/\text{Standard Value}) \quad (2)$$

As shown in equation (2), the health indicator of the range is calculated by applying floored division on the range and the standard value. The floored division gives the quotient of a division between two real numbers, i.e., "range/standard value". In the second example, range is found as 9 beats/minute, whereas the standard value is 3 beats/minute, so the health indicator is designated as the quotient of 9/3 which is +3. This way of designating a health indicator is applicable to the rest of the examples in the present disclosure when a characteristic value is based on a distance between a maximum measurement reading and a minimum measurement reading.

As a third example, the aspect of patient 110 may be the liver of patient 110, and the measurement readings of Table 1 may be utilized to designate a health indicator that serves as an indication of a health condition of the liver of patient 110. Specifically, the characteristic value for the third example may be either a range or an average of the diastolic blood pressure readings from right arm 132 of patient 110 as shown in Table 1. The range is defined as a difference between a maximum value and a minimum value among the measurement readings of column R-diastolic of Table 1, whereas the average is defined as a mean value of the maximum value and the minimum value. According to column R-diastolic of Table 1, the maximum diastolic blood pressure is 79 mmHg as measured during the fourth of the 5 measurement runs from vital sign sensor 142, and the minimum diastolic blood pressure is 71 mmHg as measured during the second of the 5 measurement runs from vital sign sensor 142. Therefore, the range is calculated as 79−71=8 mmHg, whereas the average is calculated as (79+71)/2=75 mmHg. For the third example where the aspect of interest is the liver, the standard value for the range is 3 mmHg, and the standard value for the average is 58 mmHg. The deviation of the average from the corresponding standard value may be calculated using equation (1) above to be 29% in the positive direction, and thus a corresponding health indicator is accordingly designated as +2. The health indicator of the range may be determined using equation (2) above, as the floored division of 8 mmHg and 3 mmHg, and thus designated as +2.

As a fourth example, the aspect of patient 110 may be the spleen of patient 110, and the measurement readings of Table 1 may be utilized to designate a health indicator that serves as an indication of a health condition of the spleen of patient 110. Specifically, the characteristic value for the fourth example may be either a range or an average of the diastolic blood pressure readings from left arm 131 of patient 110 as shown in Table 1. The range is defined as a difference between a maximum value and a minimum value among the measurement readings of column L-diastolic of Table 1, whereas the average is defined as a mean value of the maximum value and the minimum value. According to column L-diastolic of Table 1, the maximum diastolic blood pressure is 83 mmHg as measured during the first of the 5 measurement runs from vital sign sensor 141, and the minimum diastolic blood pressure is 74 mmHg as measured during the second and the third of the 5 measurement runs from vital sign sensor 141. Therefore, the range is calculated as 83−74=9 mmHg, whereas the average is calculated as (83+74)/2=78.5 mmHg. For the fourth example where the aspect of interest is the spleen, the standard value for the range is 3 mmHg, and the standard value for the average is 58 mmHg. The deviation of the average from the corresponding standard value may be calculated using equation (1) above, as 35% in the positive direction, and thus a corresponding health indicator is accordingly designated as +3. The health indicator of the range may be determined using equation (2) above, as the floored division of 9 mmHg and 3 mmHg, and thus designated as +3.

As a fifth example, the aspect of patient 110 may be the lung or the brain of patient 110, and the measurement readings of Table 1 may be utilized to designate a health indicator that serves as an indication of a health condition of the lung or the brain of patient 110. Specifically, the characteristic value for the fifth example may be either a range or an average of the systolic blood pressure readings from left arm 131 of patient 110 as shown in Table 1. The range is defined as a difference between a maximum value and a minimum value among the measurement readings of column L-systolic of Table 1, whereas the average is defined as a mean value of the maximum value and the minimum value. According to column L-systolic of Table 1, the maximum systolic blood pressure is 133 mmHg as measured during the first of the 5 measurement runs from vital sign sensor 141, and the minimum systolic blood pressure is 122 mmHg as measured during the fourth of the 5 measurement runs from vital sign sensor 141. Therefore, the range is calculated as 133−122=11 mmHg, whereas the average is calculated as (133+122)/2=127.5 mmHg. For the fifth example where the aspect of interest is the lung or the brain, the standard value for the range is 3 mmHg, and the standard value for the average is 100 mmHg. The deviation of the average from the corresponding standard value may be calculated using equation (1) above to be 28% in the positive direction, and thus a corresponding health indicator is accordingly designated as +2. The health indicator of the range may be determined using equation (2) above, as the floored division of 11 mmHg and 3 mmHg, and thus designated as +3.

As a sixth example, the aspect of patient 110 may be the kidney of patient 110, and the measurement readings of Table 1 may be utilized to designate a health indicator that serves as an indication of a health condition of the kidney of patient 110. Specifically, the characteristic value for the sixth example may be either a range or an average of the systolic blood pressure readings from right arm 132 of patient 110 as shown in Table 1. The range is defined as a difference between a maximum value and a minimum value among the measurement readings of column R-systolic of Table 1, whereas the average is defined as a mean value of the maximum value and the minimum value. According to column R-systolic of Table 1, the maximum systolic blood pressure is 126 mmHg as measured during the first of the 5 measurement runs from vital sign sensor 142, and the minimum systolic blood pressure is 120 mmHg as measured during the fourth of the 5 measurement runs from vital sign sensor 142. Therefore, the range is calculated as 126−120=6 mmHg, whereas the average is calculated as (126+120)/2=123 mmHg. For the sixth example where the aspect of interest is the kidney, the standard value for the range is 3 mmHg, and the standard value for the average is 100 mmHg. The deviation of the average from the corresponding standard value may be calculated using equation (1) above to be 23% in the positive direction, and thus a corresponding health indicator is accordingly designated as +2. The health indicator of the range may be determined using equation (2) above, as the floored division of 6 mmHg and 3 mmHg, and thus designated as +2.

Through the examples described above, the present disclosure provides a way of objectively evaluating a health condition of one or more aspects of a patient based on measurement readings of one or more vital signs obtained concurrently from both arms of the patient. The health condition of each of the aspects of the patient may be represented by at least one corresponding health indicator represented by an integer number. These health indicators may be analyzed by a medical practitioner, or a machine of artificial intelligence (AI), to determine or otherwise prescribe further examination, diagnosis and/or treatment based on various TCM and/or MWM principles. Combining the various health indicators designated in the examples described above, patient 110 may exhibit a disease or a sub-disease related to the heart, the spleen and the lungs, as each of the organs has a corresponding health indicator that is designated as a relatively high value of 3. According to TCM principles, concerns related to the spleen and the lungs as suggested by the high value range-based health indicators may speak of possible allergies, sub-diseases or diseases related to the respiratory system of patient 110, and concerns related to the heart and the spleen as suggested by the high value range-based health indicators may result in potential sleep problems and/or emotional stress. Moreover, concerns related to the spleen as suggested by the high value average-based health indicator may reveal issues, though possibly still in an early phase, regarding the digestive system and the immune system of patient 110.

Figure 2:
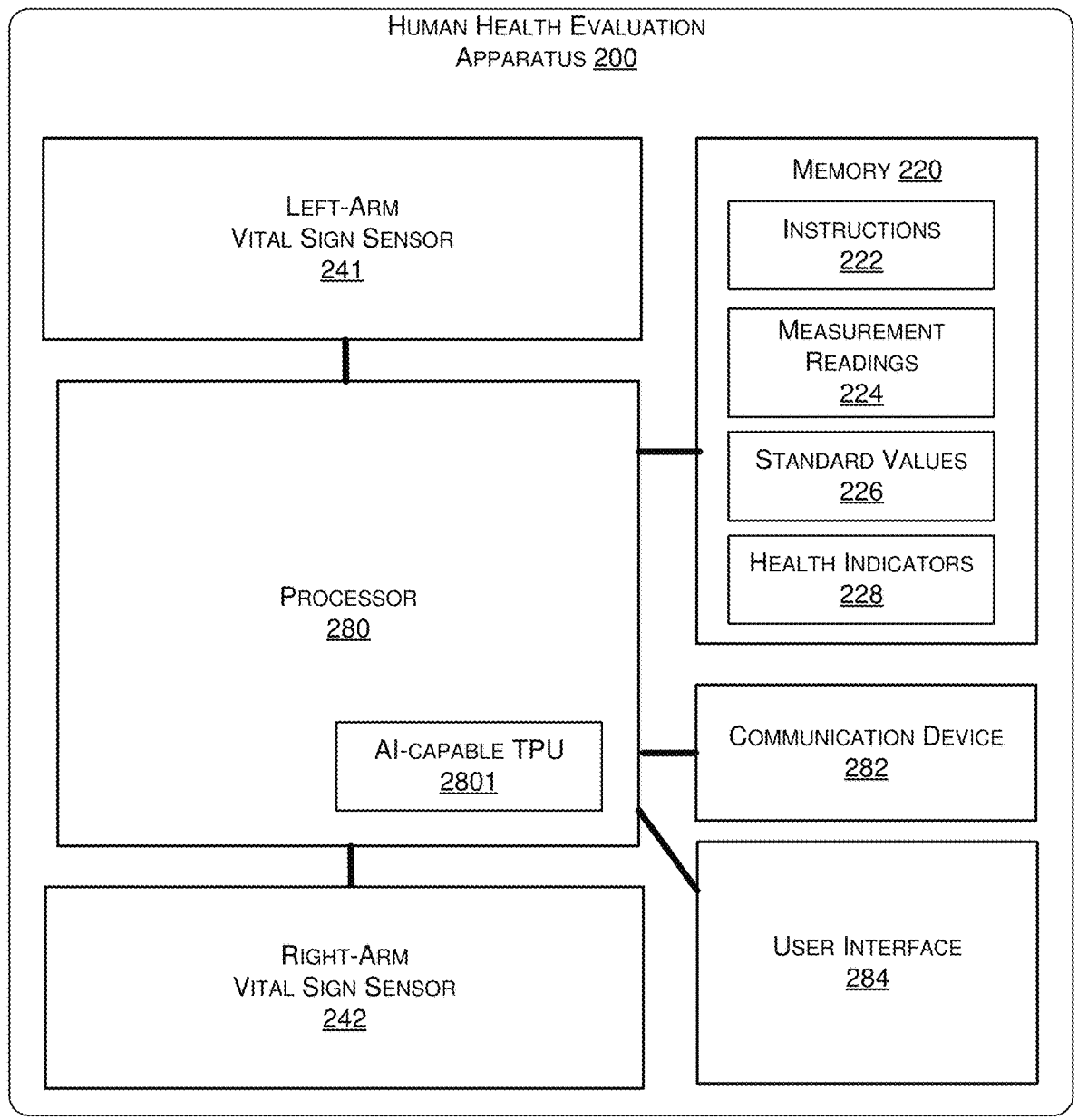
FIG. 2 is a block diagram depicting an example apparatus in accordance with an embodiment of the present disclosure.

FIG. 2 illustrates an example apparatus, or human health evaluation apparatus 200, in accordance with an embodiment of the present disclosure. Apparatus 200 may perform various functions related to techniques, methods and systems described herein, including those described above in the first, second, third, fourth, fifth and sixth examples, as well as those described below with respect to process 300 of FIG. 3. Apparatus 200 may include at least some of the components illustrated in FIG. 2.

Referring to FIG. 2, human health evaluation apparatus 200 may include processor 280 and memory 220. Memory 220 may store measurement readings 224 that may be obtained by vital sign sensors 141 and 142 of FIG. 1, standard values 226 for the range and the average of each of the first through sixth examples described above, as well as health indicators 228 as designated in the above examples. Memory 220 may also store one or more sets of instructions 222 for processor 280 to execute and perform the various obtaining, calculating and designating operations as described above in the present disclosure, including those performed in the first through sixth examples described above.

In some embodiments, apparatus 200 may include a left-arm vital sign sensor 241 (such as vital sign sensor 141 of FIG. 1) and a right-arm vital sign sensor 242 (such as vital sign sensor 142 of FIG. 1) for obtaining measurement readings 224 of vital signs of a patient, such as a pulse rate, a systolic blood pressure, or a diastolic blood pressure of patient 110 of FIG. 1. In some embodiments, apparatus 200 may also include a communication device 282 (such as wireless transceiver 182 of FIG. 1) capable of wirelessly transmitting and receiving data. For example, communication device 282 may be used by processor 280 to remotely access a data server and update standard values 226 stored in memory 220. Communication device 282 may also be used by processor 280 to transmit health indicators 228, as designated by processor 280, to a medical practitioner located at a remote location. In some embodiments, apparatus 200 may further include a user interface 284 (such as communication console 184 of FIG. 1) for communicating with the patient or a local medical practitioner.

In some embodiments, processor 280 of apparatus 200 may include a tensor processing unit (TPU) 2801 that is capable for developing AI that practices TMC principles or MWM principles. TPU 2801 may exercise a self-training capability of the AI using data stored in memory 220 and feedback from a human medical practitioner to refine or update standard values 226 and even improve an algorithm of designating health indicators 228.

Figure 3:
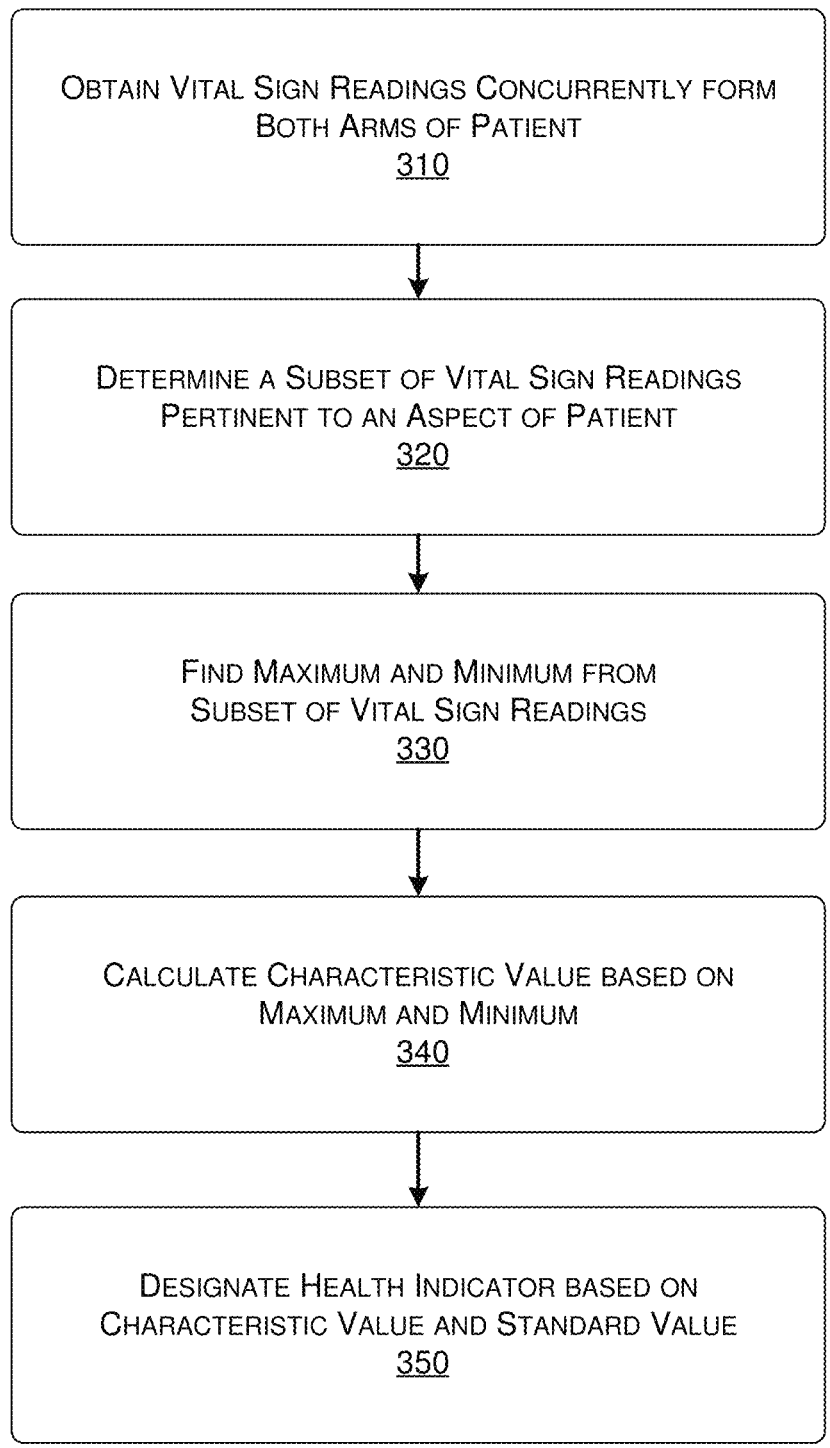
FIG. 3 is a flowchart depicting an example process in accordance with an embodiment of the present disclosure.

FIG. 3 illustrates an example process 300, in accordance with the present disclosure, for evaluating a health condition of an aspect of a patient. Process 300 may include one or more operations, actions, or functions shown as blocks such as 310, 320, 330, 340, and 350. Although illustrated as discrete blocks, various blocks of process 300 may be divided into additional blocks, combined into fewer blocks, or eliminated, depending on the desired implementation. Process 300 may be realized by human health evaluation apparatus 200 of FIG. 2. In addition, process 300 may be utilized in implementation 100 of FIG. 1 to carry out the first through sixth examples described above. Process 300 may begin with block 310.

At 310, process 300 may involve a processor (such as processor 180 of FIG. 1 or processor 280 of FIG. 2) concurrently obtaining vital sign readings (such as the measurement readings of one or more vital signs of implementation 100 or measurement readings 224 of apparatus 200) from both arms of a patient (such as arms 131 and 132 of patient 110). The vital sign readings may be obtained via vital sign sensors 141 and 142 of FIG. 1 or vital sign sensors 241 and 242 of FIG. 2. Process 300 may proceed from 310 to 320.

At 320, process 300 may involve the processor determining a subset of the vital sign readings that is pertinent to an aspect of the patient. For example, in the third example described above, the aspect of interest is the heart of the patient, and the subset of the vital sign readings includes the readings of diastolic blood pressure obtained from the right arm of the patient. Process 300 may proceed from 320 to 330.

At 330, process 300 may involve the processor finding a maximum reading and a minimum reading from the subset of the vital sign readings. Still illustrated using the third example, the maximum diastolic blood pressure is 79 mmHg as measured during the fourth of the 5 measurement runs from vital sign sensor 142, and the minimum diastolic blood pressure is 71 mmHg as measured during the second of the 5 measurement runs from vital sign sensor 142, as shown in Table 1. Process 300 may proceed from 330 to 340.

At 340, process 300 may involve the processor calculating a characteristic value based on the maximum reading and the minimum reading. In the third example described above, a characteristic value, i.e., the average of the maximum reading and the minimum reading, is calculated to be 75 mmHg. Process 300 may proceed from 340 to 350.

At 350, process 300 may involve the processor designating a health indicator based on the characteristic value and a standard value, the health indicator being an indication of the health condition of the aspect of the patient. In the third example above, a health indicator is designated based on a standard value of 58 mmHg and the average-based characteristic value of 75 mmHg. Specifically, a deviation is calculated using equation (1) as 29% in the positive direction, and the health indicator is accordingly designated as +2, indicating certain concerns of the health condition of the heart of patient 110.

The present disclosure has been described in sufficient details with a certain degree of particularity. It is understood to those skilled in the art that the present disclosure of embodiments has been made by way of examples only and that numerous changes in the arrangement and combination of parts may be resorted without departing from the spirit and scope of the present disclosure as claimed. Accordingly, the scope of the present disclosure is defined by the appended claims rather than the foregoing description of embodiments.

Additional Notes

The herein-described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Further, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Moreover, it will be understood by those skilled in the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various implementations of the present disclosure have been described herein for purposes of illustration, and that various modifications may be made without departing from the scope and spirit of the present disclosure. Accordingly, the various implementations disclosed herein are not intended to be limiting, with the true scope and spirit being indicated by the following claims.

What is claimed is:

1. A method of evaluating a health condition of a patient, comprising:
 obtaining, by a first vital sign sensor disposed on a left arm of the patient and a second vital sign sensor disposed on a right arm of the patient, measurement readings of a pulse rate, a systolic blood pressure and a diastolic blood pressure concurrently taken from both the left arm and the right arm for a successive plurality of times;
 calculating an overall characteristic value of the patient based on a ratio of at least one of the measurement readings of the systolic blood pressure to at least one of the measurement readings of the diastolic blood pressure;
 calculating a first characteristic value of a heart of the patient based on a difference between a maximum value and a minimum value of the measurement readings of the pulse rate obtained from both the left and right arms;
 calculating a first characteristic value of a liver of the patient based on a difference between a maximum value and a minimum value of the measurement readings of the diastolic blood pressure obtained from the right arm;
 calculating a first characteristic value of a spleen of the patient based on a difference between a maximum value and a minimum value of the measurement readings of the diastolic blood pressure obtained from the left arm;
 calculating a first characteristic value of a lung or a brain of the patient based on a difference between a maximum value and a minimum value of the measurement readings of the systolic blood pressure obtained from the left arm;
 calculating a first characteristic value of a kidney of the patient based on a difference between a maximum value and a minimum value of the measurement readings of the systolic blood pressure obtained from the right arm;
 designating an overall health indicator based on the overall characteristic value and an overall standard value;
 designating a first health indicator of the heart based on the first characteristic value of the heart and a first standard value of the heart;
 designating a first health indicator of the liver based on the first characteristic value of the liver and a first standard value of the liver;
 designating a first health indicator of the spleen based on the first characteristic value of the spleen and a first standard value of the spleen;
 designating a first health indicator of the lung or the brain based on the first characteristic value of the lung or the brain and a first standard value of the lung or the brain;
 designating a first health indicator of the kidney based on the first characteristic value of the kidney and a first standard value of the kidney; and
 transmitting, by a communication device, the overall health indicator, the first health indicator of the heart, the first health indicator of the liver, the first health indicator of the spleen, the first health indicator of the lung or the brain and the first health indicator of the kidney.

2. The method of claim 1, further comprising:
 calculating a second characteristic value of the heart based on an average of the maximum value and the minimum value of the measurement readings of the pulse rate obtained from both the left and right arms;
 calculating a second characteristic value of the liver based on an average of the maximum value and the minimum value of the measurement readings of the diastolic blood pressure obtained from the right arm;
 calculating a second characteristic value of the spleen based on an average of the maximum value and the minimum value of the measurement readings of the diastolic blood pressure obtained from the left arm;
 calculating a second characteristic value of the lung or the brain based on an average of the maximum value and the minimum value of the measurement readings of the systolic blood pressure obtained from the left arm;
 calculating a second characteristic value of the kidney based on an average of the maximum value and the minimum value of the measurement readings of the systolic blood pressure obtained from the right arm;
 designating a second health indicator of the heart based on the second characteristic value of the heart and a second standard value of the heart;
 designating a second health indicator of the liver based on the second characteristic value of the liver and a second standard value of the liver;
 designating a second health indicator of the spleen based on the second characteristic value of the spleen and a second standard value of the spleen;
 designating a second health indicator of the lung or the brain based on the second characteristic value of the lung or the brain and a second standard value of the lung or the brain;
 designating a second health indicator of the kidney based on the second characteristic value of the kidney and a second standard value of the kidney; and
 transmitting, by the communication device, the second health indicator of the heart, the second health indicator of the liver, the second health indicator of the spleen, the second health indicator of the lung or the brain and the second health indicator of the kidney.

3. The method of claim 2, wherein:
 the overall standard value is 1.72,
 the first standard value of the heart is 3 beats per minute,
 each of the first standard value of the liver, the first standard value of the spleen, the first standard value of the lung or the brain and the first standard value of the kidney is 3 millimeter of mercury (mmHg),
 the second standard value of the heart is 65 beats per minute,
 each of the second standard value of the liver and the second standard value of the spleen is 58 mmHg, and
 each of the second standard value of the lung or the brain and the second standard value of the kidney is 100 mmHg.

4. An apparatus, comprising:
 a left-arm vital sign sensor capable of successively taking a first plurality of measurement readings of a vital sign from a left arm of a patient;
 a right-arm vital sign sensor capable of successively taking a second plurality of measurement readings of the vital sign from a right arm of the patient;

a communication device capable of transmitting a health indicator and receiving one or more standard values;

a memory capable of storing one or more sets of instructions and the one or more standard values; and a processor configured to execute the one or more sets of instructions stored in the memory such that, upon executing the one or more sets of instructions, the processor performs operations comprising:

receiving the one or more standard values via the communication device;

obtaining the first plurality of measurement readings and the second plurality of measurement readings concurrently via the left-arm vital sign sensor and the right-arm vital sign sensor;

calculating a characteristic value based on measurement data comprising either or both of the first plurality of measurement readings and the second plurality of measurement readings, the characteristic value comprising a difference between a maximum value and a minimum value of the measurement data;

designating the health indicator by applying a floored division on the characteristic value and at least one of the one or more standard values, the health indicator being an indication of a health condition of an aspect of the patient; and transmitting the health indicator via the communication device.

5. The apparatus of claim 4, wherein the aspect comprises a heart, a liver, a spleen, a lung, a brain, or a kidney, and wherein:

in an event that the aspect comprises the heart:
the vital sign comprises a pulse rate, and
the measurement data comprises both of the first plurality of measurement readings and the second plurality of measurement readings, in an event that the aspect comprises the liver:
the vital sign comprises a diastolic blood pressure, and
the measurement data comprises the second plurality of measurement readings, in an event that the aspect comprises the spleen:
the vital sign comprises a diastolic blood pressure, and
the measurement data comprises the first plurality of measurement readings, in an event that the aspect comprises the lung or the brain:
the vital sign comprises a systolic blood pressure, and
the measurement data comprises the first plurality of measurement readings, and in an event that the aspect comprises the kidney:
the vital sign comprises a systolic blood pressure, and
the measurement data comprises the second plurality of measurement readings.

6. The apparatus of claim 4, wherein the one or more standard values comprise 3 beats per minute or 3 millimeter of mercury (mmHg).

* * * * *